(12) United States Patent
Trieu et al.

(10) Patent No.: US 8,372,126 B2
(45) Date of Patent: Feb. 12, 2013

(54) SURGICAL FASTENERS WITH MECHANICAL AND OSTEOGENIC FIXATION MEANS

(75) Inventors: Hai H. Trieu, Cordova, TN (US); Jon Carl Serbousek, Memphis, TN (US); Michael S. Veldman, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 294 days.

(21) Appl. No.: 11/408,314

(22) Filed: Apr. 21, 2006

(65) Prior Publication Data
US 2007/0270858 A1 Nov. 22, 2007

(51) Int. Cl.
*A61B 17/04* (2006.01)
(52) U.S. Cl. .......................................... 606/304; 606/76
(58) Field of Classification Search .................. 606/60, 606/65, 72–77, 300–331; 411/914
See application file for complete search history.

(56) References Cited

U.S. PATENT DOCUMENTS

| | | | | |
|---|---|---|---|---|
| 4,653,489 A | * | 3/1987 | Tronzo | 606/65 |
| 5,098,434 A | * | 3/1992 | Serbousek | 606/308 |
| 5,112,133 A | | 5/1992 | Kurosawa et al. | |
| 5,122,114 A | * | 6/1992 | Miller et al. | 604/506 |
| 5,360,448 A | * | 11/1994 | Thramann | 606/60 |
| 5,462,990 A | | 10/1995 | Hubbell et al. | |
| 5,514,137 A | * | 5/1996 | Coutts | 606/62 |
| 5,567,440 A | | 10/1996 | Hubbell et al. | |
| 5,627,233 A | * | 5/1997 | Hubbell et al. | 525/54.1 |
| 5,743,912 A | | 4/1998 | Lahille et al. | |
| 5,871,484 A | * | 2/1999 | Spievack et al. | 606/60 |
| 5,885,287 A | | 3/1999 | Bagby | |
| 6,048,343 A | * | 4/2000 | Mathis et al. | 606/916 |
| 6,214,012 B1 | | 4/2001 | Karpman et al. | |
| 6,554,830 B1 | | 4/2003 | Chappius | |
| 6,565,572 B2 | | 5/2003 | Chappius | |
| 6,743,521 B2 | | 6/2004 | Hubbell et al. | |
| 6,814,734 B2 | * | 11/2004 | Chappuis et al. | 606/80 |
| 7,250,055 B1 | * | 7/2007 | Vanderwalle | 606/92 |
| 7,608,097 B2 | * | 10/2009 | Kyle | 606/304 |
| 7,615,070 B2 | * | 11/2009 | Biscup | 606/322 |
| 7,850,717 B2 | * | 12/2010 | Dewey et al. | 606/246 |
| 2001/0021852 A1 | * | 9/2001 | Chappius | 606/73 |

(Continued)

FOREIGN PATENT DOCUMENTS

| | | |
|---|---|---|
| WO | WO 98/47948 | 10/1998 |
| WO | WO 99/10022 | 3/1999 |

(Continued)

OTHER PUBLICATIONS

"International Search Report," International Application No. PCT/US2007/066015, Jan. 25, 2008, European Patent Office, Rijswijk, Netherlands.

*Primary Examiner* — Thomas Barrett
*Assistant Examiner* — Melissa A Golob

(57) ABSTRACT

Surgical fasteners that combine mechanical and osteogenic means of fixation to maximize in vivo stability and long-term performance. The fastener generally includes a head and a shaft. The fastener is fenestrated and includes a channel that leads into one or more openings along the shaft. Bone void filling materials is delivered through the channel to the shaft to improve anchoring. In one embodiment, the osteogenic means comprise a coating applied to the fastener to improve bony apposition. The fastener with combined mechanical and osteogenic means provides initial, immediate anchoring and long term anchoring.

18 Claims, 5 Drawing Sheets

U.S. PATENT DOCUMENTS

| | | | |
|---|---|---|---|
| 2003/0083662 A1* | 5/2003 | Middleton | 606/72 |
| 2004/0225292 A1* | 11/2004 | Sasso et al. | 606/73 |
| 2005/0059972 A1* | 3/2005 | Biscup | 606/73 |
| 2005/0084513 A1 | 4/2005 | Tang | |
| 2005/0113936 A1 | 5/2005 | Brustad et al. | |
| 2005/0137707 A1 | 6/2005 | Malek | |
| 2005/0143823 A1* | 6/2005 | Boyd et al. | 623/17.16 |
| 2005/0159748 A1 | 7/2005 | Clark | |
| 2006/0036253 A1 | 2/2006 | Leroux et al. | |
| 2007/0233071 A1* | 10/2007 | Dewey et al. | 606/61 |

FOREIGN PATENT DOCUMENTS

| | | |
|---|---|---|
| WO | 00/28907 | 5/2000 |
| WO | 01/54561 | 8/2001 |
| WO | WO 0154561 A2 * | 8/2001 |
| WO | WO 03/072156 A1 | 9/2003 |
| WO | 2005/102191 | 11/2005 |
| WO | 2006/031397 | 3/2006 |

* cited by examiner

SURGICAL FASTENERS WITH MECHANICAL AND OSTEOGENIC FIXATION MEANS

BACKGROUND

The present application is directed to surgical fasteners for attachment within a patient and, more specifically, to surgical fasteners including mechanical and osteogenic means to enhance short term and long term anchoring.

The spine is divided into four regions comprising the cervical, thoracic, lumbar, and sacrococcygeal regions. The cervical region includes the top seven vertebral members identified as C1-C7. The thoracic region includes the next twelve vertebral members identified as T1-T12. The lumbar region includes five vertebral members L1-L5. The sacrococcygeal region includes nine fused vertebral members that form the sacrum and the coccyx. The vertebral members of the spine are aligned in a curved configuration that includes a cervical curve, thoracic curve, and lumbosacral curve.

Various types of implants may be implanted within a patient for various functions including to support one or more vertebral members, replace a vertebral member and/or intervertebral disc, provide motion, or strengthen the spine. Examples of implants include rods, plates, and intervertebral members.

Fasteners are used to attach the implants to the vertebral members. The fasteners may include a first section that attaches within one of the vertebral members, and a second section that engages the implant. The fasteners should attach to the vertebral member and provide a strong anchor for maintaining the position of the implant. The fasteners may provide for immediate short term anchoring at the time of insertion, and also may provide for long term anchoring over the life of the implant.

SUMMARY

The present application discloses various embodiments of surgical fasteners that combine mechanical and osteogenic means of fixation to maximize in vivo stability and long-term performance. The fastener generally includes a head and a shaft. The fastener is fenestrated and includes a channel that leads into one or more openings along the shaft. Bone void filling material is delivered through the channel to one or more sections along the shaft to improve anchoring. In one embodiment, the osteogenic means comprise a coating applied to the fastener to improve bony apposition. The fastener with combined mechanical and osteogenic means provides initial, immediate anchoring and long term anchoring.

DETAILED DESCRIPTION

The present application is directed to surgical fasteners that combine mechanical and osteogenic means of fixation. The fastener includes a channel that leads into one or more openings along the shaft. Bone void filling material is delivered through the channel and openings to improve anchoring to the vertebral member. The fastener may further include a osteogenic means to improve bony apposition. The fastener with combined mechanical and osteogenic means provides initial immediate anchoring and long term anchoring.

Figure 1:
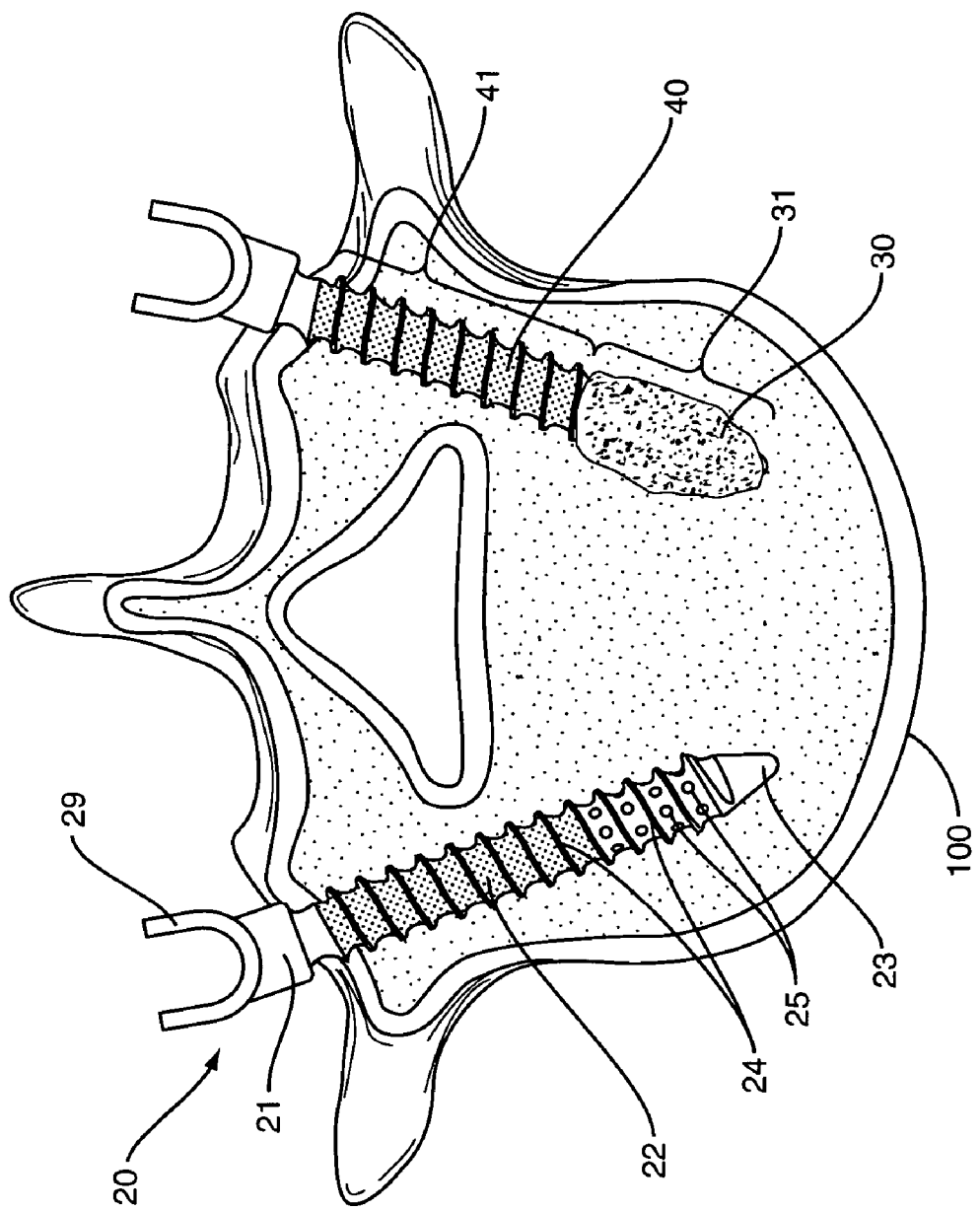
FIG. 1 is a cross section view illustrating a vertebral member with a pair of fasteners according to one embodiment.

FIG. 1 illustrates one embodiment of fasteners, generally illustrated as 20, mounted within a vertebral member 100. In this embodiment, each of the fasteners 20 is substantially the same although it is understood that embodiments with multiple fasteners 20 may include different types of fasteners 20. The fasteners 20 of FIG. 1 include a head 21 at a proximal end and a shaft 22 that terminates at a tip 23 at a distal end. Threads 24 extend along the shaft 22 and bite into the vertebral member 100 during insertion. The head 21 extends outward from the vertebral member 100. In this embodiment, a saddle 29 is attached to the head 21 to receive a vertebral rod (not illustrated).

Figure 2:
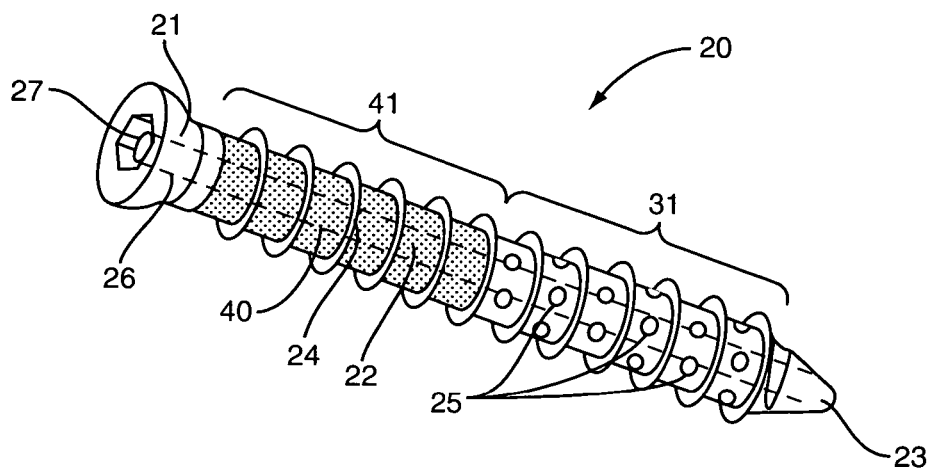
FIG. 2 is a perspective view illustrating a fastener according to one embodiment.

FIG. 2 illustrates a channel 26 that extends from an inlet 27 within the head 21 towards the tip 23. Channel 26 may extend the entire length of the fastener 20, or may terminate inward from the tip 23. Openings 25 are in communication with the channel 26 and positioned within a bone void filling section 31 of the shaft 22. In this embodiment, the bone void filling section 31 with the openings 25 is positioned at the distal end of the fastener 20. The openings 25 may be positioned about the periphery of the shaft 22 to distribute the bone void filling material 30 around the outer surface of the shaft 22. The number and size of the openings 25 may vary depending upon the context of use. Openings 25 may also be positioned at or spaced away from the tip 23. Embodiments of fenestrated surgical fasteners are disclosed in U.S. Pat. Nos. 6,554,830 and 6,565,572, each incorporated herein by reference.

The bone void filling section 31 is arranged along the shaft 22 to be positioned within an interior of the vertebral member 100. The bone void filling material 30 improves the connection and strength of anchoring where the fastener 20 contacts cancellous bone tissue. Bone void filling material 30 is particularly effective for weakened bones such as in elderly rheumatoid or osteoporitic patients. The bone void filling material 30 is expelled through the openings 25 and surrounds the bone void filling section 31 of the shaft 22. Contact with surrounding soft tissues is minimized or eliminated because the bone void filling material 30 is confined to the space in the cancellous bone tissue.

A variety of bone void filling materials 30 may be used to anchor the fastener 20. Examples of bone void filling material 30 include bone cement, polymethylmethacrylate (PMMA), calcium phosphate (CaP), demineralized bone matrix (DBM), bi-calcium phosphate matrix, platelet gel, autograft, allograft, bone morphogenetic protein (BMP) in a carrier matrix, calcium phosphate-based materials, methomathactuloid, cranial plast, ceramics, polymers, calcium-sulfate, or one or more of the previous in combination.

A osteogenic section 41 of the shaft 22 includes a osteogenic material 40. The osteogenic material 40 improves the connection with the cortical bone tissue at the outer shell of the vertebral member 100. The osteogenic material 40 may be positioned to contact the cortical bone tissue or the cortical and cancellous bone tissues. FIGS. 1 and 2 include embodiments with the osteogenic section 41 positioned along a proximal section of the shaft 22. The osteogenic material 41 is positioned along an enlarged portion of the shaft 22 to contact the cortical bone tissue at the exterior of the vertebral member 100, in addition to the cancellous bone tissue within an interior.

The osteogenic material 40 is attached to the fastener 20 to improve bony apposition with the vertebral member 100. The osteogenic material 40 may be osteo-compatible, and may be osteo-conductive and/or osteo-inductive. The material 40 may be heterogenous or homogeneous. Examples of osteogenic materials 40 include hydroxyapatite, osteoinductive matters such as BMP, LIM mineralized proteins (LMP), osteoindiuctive peptides, growth factors, pharmaceutical agents such as antibiotics, pain medication, anti-inflammatory drugs, steroids, osteogenic compositions such as transforming growth factor β1, insulin-like growth factor 1, platelet-derived growth factor, fibroblast growth factor, therapeutic or infection resistant agent, or one or more of the previous in combination.

In one embodiment, the osteogenic material 40 may include multifunctional polymeric materials that inhibit adhesion and immune recognition between cells and tissue. The materials may include a tissue-binding component and a tissue non-binding component. Specific materials may include PEG/PLL copolymers with molecular weights greater than 300, with structures that include AB copolymers, ABA copolymers, and brush-type copolymers. U.S. Pat. Nos. 5,462,990 and 5,627,233 disclose various materials and are incorporated herein by reference.

The osteogenic material 40 may use a grafted polyionic copolymers that are able to attach to biological and non-biological samples to control cell-surface, cell-cell, and tissue-surface interactions as disclosed in WO 98/47948 incorporated herein by reference. Material 40 may also include the application of polyionic, PEG-grafted copolymers such as disclosed in U.S. Pat. No. 6,743,521, incorporated herein by reference.

In one embodiment, the material 40 contains an appropriate amount of grafted non-interactive material such as PEG (polyethylene glycol) or PEO (polyethylene oxide) within the polymer. Another preferred example is a device, wherein the polymer is a PEG-grafted poly (amino acid) with a polycationic backbone made of lysine, histidine, arginine or ornithine in D-, L- or DL configuration, or the polymer is a PEG-grafted polymer with a cationic backbone of a polysaccharide such as chitosan, partially deacetylated chitin, and amine-containing derivatives of neutral polysaccharides, or the polymer is a PEG-grafted non-peptide polyamine with a polycationic backbone such as poly (aminostyrene), poly (aminoacrylate), poly (N-methyl aminoacrylate), poly (N-ethylaminoacrylate), poly (N,N-dimethyl aminoacrylate), poly (N,N-diethylaminoacrylate), poly (aminomethacrylate), poly (N-methyl amino-methacrylate), poly (N-ethyl aminomethacrylate), poly (N,N-dimethyl aminomethacrylate), poly (N,N-diethyl aminomethacrylate), poly (ethyleneimine), polymers of quaternary amines, such as poly (N,N,N-trimethylaminoacrylate chloride), poly (methacrylamidopropyltrimethyl ammonium chloride), or the polymer is a PEG-grafted charged synthetic polymer with a polycationic backbone such as polyethyleneimine, polyamino(meth)acrylate, polyaminostyrene, polyaminoethylene, poly (aminoethyl)ethylene, polyaminoethylstyrene, and N-alkyl derivatives thereof.

Another preferred example is a device, wherein the copolymer is a PEG-grafted copolymer with an anionic backbone of a poly (amino acid) grafted with poly (ethylene glycol) where the amino acid contains an additional pendant carboxy group imparting a negative charge to the backbone at pH above 4 and in particular at neutral pH such as polyaspartic acid or polyglutamic acid; or a natural or unnatural polymer with pendant negatively charged groups, particularly carboxylate groups, including alginate, carrageenan, furcellaran, pectin, xanthan, hyaluronic acid, heparin, heparan sulfate, chondroitin sulfate, dermatan sulfate, DEXTRAN sulfate, poly (meth) acrylic acid, oxidized cellulose, carboxymethyl cellulose and crosmarmelose, synthetic polymers and copolymers containing pendant carboxyl groups, such as those containing maleic acid or fumaric acid in the backbone. Examples of these materials are disclosed in U.S. Patent No 5,567,440, herein incorporated by reference.

The osteogenic material 40 may use a coating of nanoparticles, wherein each particle is generally less than 500 nm in diameter. The nanoparticles may reduce protein "denaturation" as well as subsequent foreign body reactions. Nanoparticles may include a metal particle, carbon particle, inorganic chemical particle, organic chemical particle, ceramic particle, graphite particle, polymer particle, protein particle, peptide particle, DNA particle, RNA particle, bacteria/virus particle, hydrogel particle, liquid particle or porous particle. Thus, the nanoparticles may be, for example, metal, carbon, graphite, polymer, protein, peptide, DNA/RNA, microorganisms (bacteria and viruses) and polyelectrolyte. Polymers may include copolymers of water soluble polymers, including, but not limited to, DEXTRAN, derivatives of poly-methacrylamide, PEG, maleic acid, malic acid, and maleic acid anhydride and may include these polymers and a suitable coupling agent, including 1-ethyl-3(3-dimethylaminopropyl)-carbodiimide, also referred to as carbodiimide. Polymers may be degradable or nondegradable or of a polyelectrolyte material. Degradable polymer materials include poly-L-glycolic acid (PLGA), poly-DL-glycolic, poly-L-lactic acid (PLLA), PLLA-PLGA copolymers, poly(DL-lactide)-block-m- ethoxy polyethylene glycol, polycaprolacton, poly (caprolacton)-block-metho- xy polyethylene glycol (PCL-MePeg), poly(DL-lactide-co -caprolactone)-block--methoxy polyethylene glycol (PDLLACL-MePEG), some polysaccharide (e.g., hyaluronic acid, polyglycan, chitoson), proteins (e.g., fibrinogen, albumin, collagen, extracellular matrix), peptides (e.g., RGD, polyhistidine), nucleic acids (e.g., RNA, DNA, single or double stranded), viruses, bacteria, cells and cell fragments, organic or carbon-containing materials, as examples. Nondegradable materials include natural or synthetic polymeric materials (e.g., polystyrene, polypropylene, polyethylene teraphthalate, polyether urethane, polyvinyl chloride, silica, polydimethyl siloxane, acrylates, arcylamides, poly (vinylpyridine), polyacroleine, polyglutaraldehyde), some polysaccharides (e.g., hydroxypropyl cellulose, cellulose derivatives, DEXTRAN.RTM., dextrose, sucrose, FICOLL. RTM., PERCOLL. RTM., arabinogalactan, starch), and hydrogels (e.g., polyethylene glycol, ethylene vinyl acetate, N-isopropylacrylamide, polyamine, polyethyleneimine, poly-aluminuin chloride). U.S. Patent Application Publication No. 2005/0084513 discloses various nanoparticles and is herein incorporated by reference.

The osteogenic material 40 may be attached to the shaft 22 in a variety of manners such as a coating applied to the exterior of the shaft 22, or impregnated within the shaft material. The osteogenic material 40 may be applied at a point prior to the surgical procedure, or may be applied during the time of the surgical procedure. In one example, the osteogenic material 40 is a paste that is attached to the shaft 22 immediately prior to attachment into the vertebral member 100.

Figure 3:
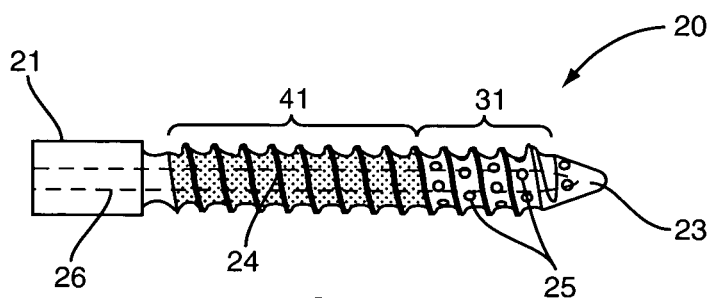
FIG. 3 is a side view illustrating a fastener according to one embodiment.
Figure 4:
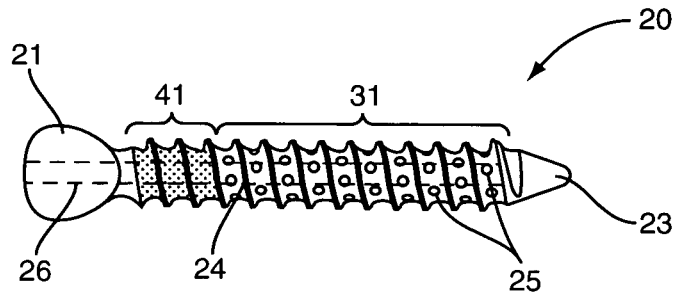
FIG. 4 is a side view illustrating a fastener according to one embodiment.
Figure 5:
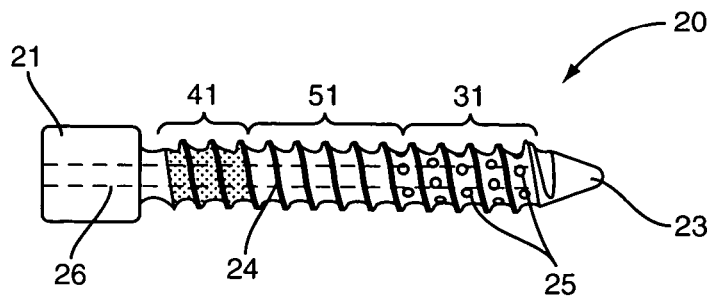
FIG. 5 is a side view illustrating a fastener according to one embodiment.

The osteogenic material 40 may be applied over the entirety or a portion of the osteogenic section 41. The lengths and positioning of the osteogenic section 41 along the shaft 22 may vary. FIG. 2 illustrates an embodiment with the osteogenic section 41 approximately equal in length to the bone void filling section 31. FIG. 3 illustrates an embodiment with a larger osteogenic section 41, and FIG. 4 illustrates a smaller osteogenic section 41 each defined relative to the bone void filling section 31. FIG. 5 illustrates an embodiment with the bone void filling and osteogenic sections 31, 41 being spaced apart. A third section 51 void of openings 25 or osteogenic material 40 separates the bone void filling and osteogenic sections 31, 41.

Figure 6:
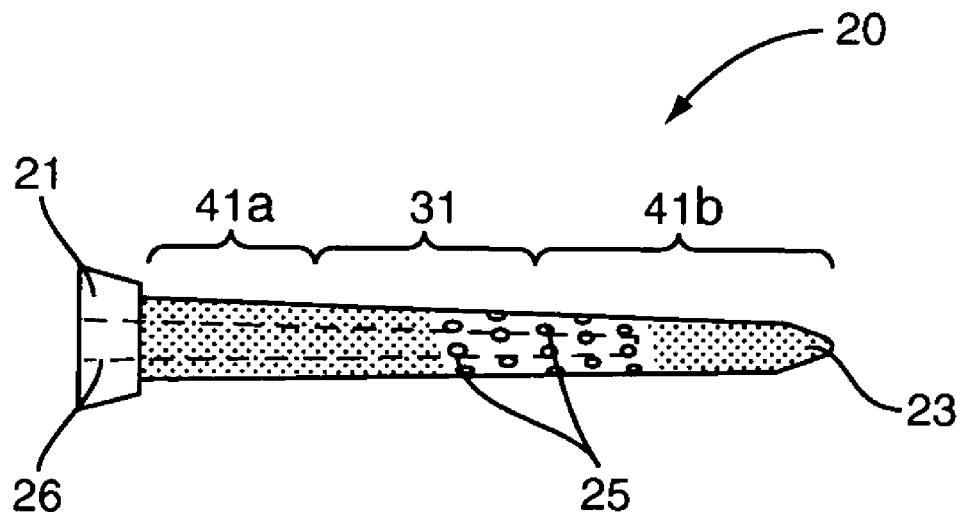
FIG. 6 is a side view illustrating a fastener according to one embodiment.

In some embodiments, two or more different osteogenic materials 40 are attached to the shaft 22. The different osteogenic materials 40 may be positioned along the same section of the shaft 22, or may be separated. FIG. 6 illustrates an embodiment with a first osteogenic section 41a separated from a second osteogenic section 41b. The amount of separation may vary. In this embodiment, a bone void filling section 31 is positioned between the osteogenic sections 41a, 41b.

Figure 7:
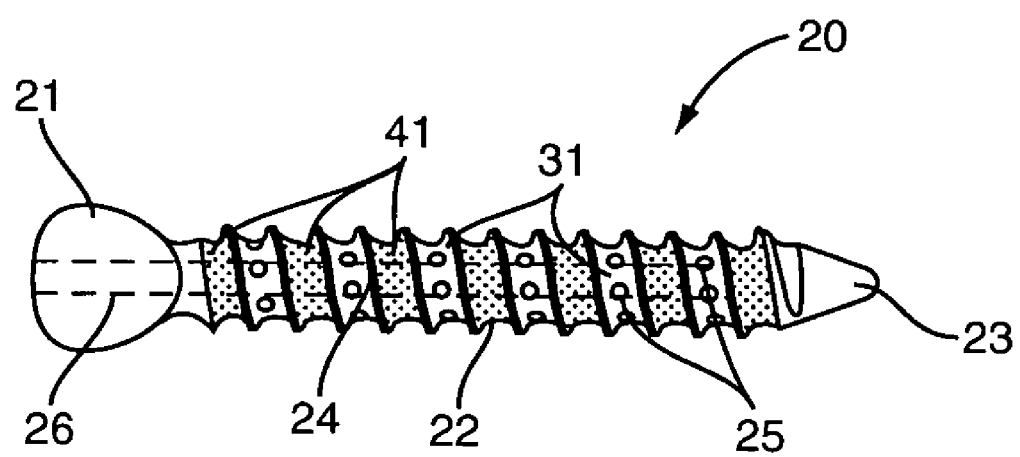
FIG. 7 is a side view illustrating a fastener according to one embodiment.

Bone void filling sections 31 and osteogenic sections 41 may be interspersed along the length of the shaft 22. FIG. 7 illustrates one embodiment with helical bone void filling and osteogenic sections 31, 41 that are spaced along the shaft 22.

The bone void filling material 30 and/or the osteogenic material 40 may further include therapeutic or pharmaceutical agents that provide in vivo release of these agents. Such agents may include, but are not limited to, antibiotics, analgesics, anesthetics, anti-inflammatory drugs, steroids, antiviral and anti-retroviral compounds, growth factors, therapeutic proteins or peptides, therapeutic nucleic acids, and combinations thereof. Various agents are disclosed in U.S. Patent Application Publication No. 2006/0047341 herein incorporated by reference.

Figure 8A:
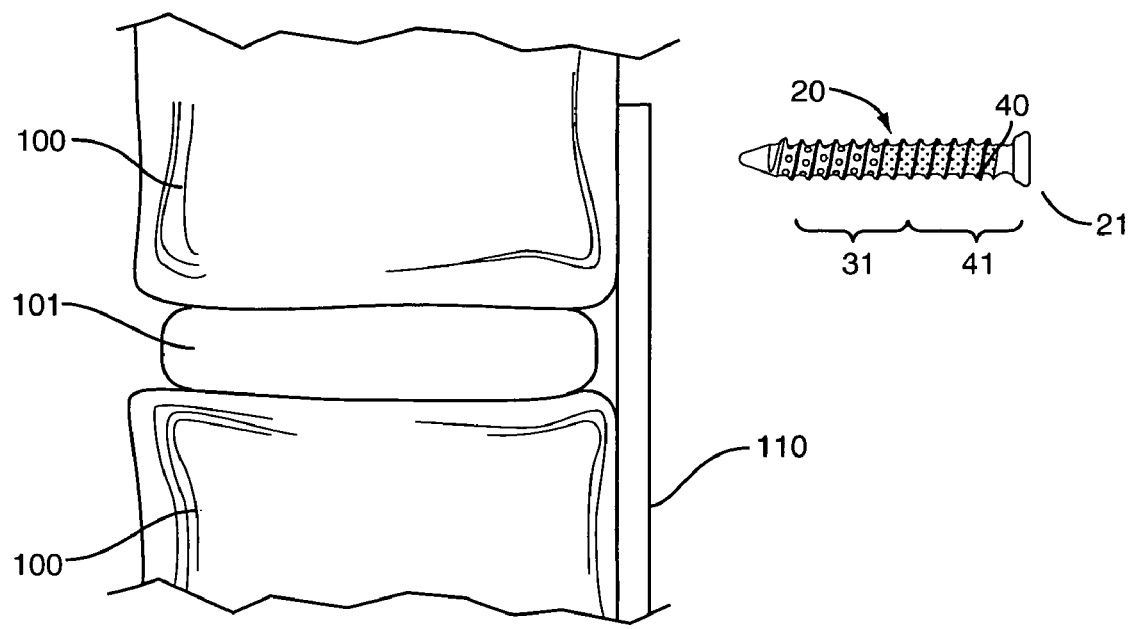
FIGS. 8A-D are side views illustrating a method of attaching a fastener within a vertebral member according to one embodiment.
Figure 8B:
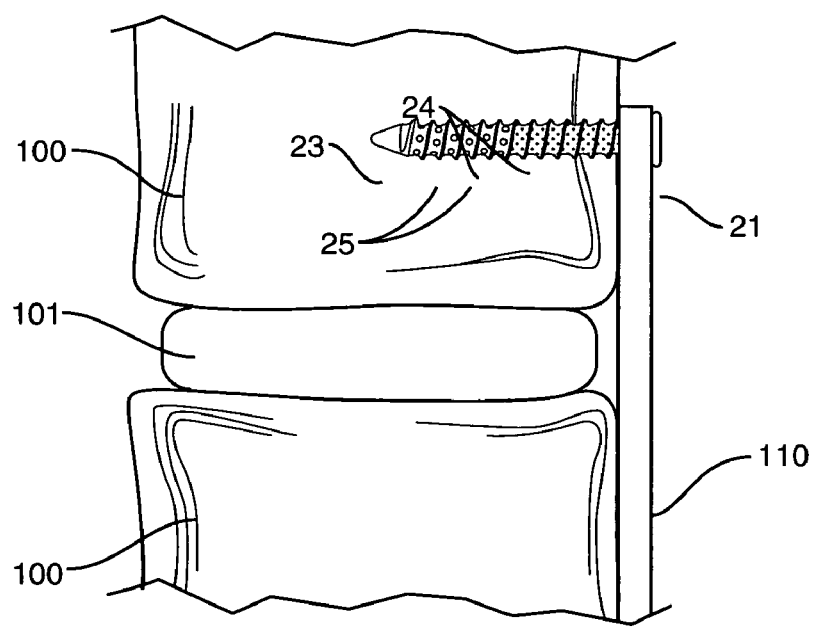

FIGS. 8A-8D illustrate one method of attaching a fastener 20 to a vertebral member 100. Fastener 20 is used for attached a plate 110 that extends across an intervertebral disc 101 positioned between adjacent vertebral members 100. The fastener 20 in this embodiment includes a bone void filling section 31 at the distal end. The osteogenic material 40 of section 41 includes a hydroxyapatite coating applied to a proximal section of the shaft 22. The fastener 20 is inserted into the vertebral member 100. The threads 24 bite into the vertebral member 100 and upon full insertion an underside of the head 21 is in contact with the surface of the implant 110 as illustrated in FIG. 8B.

Figure 8C:
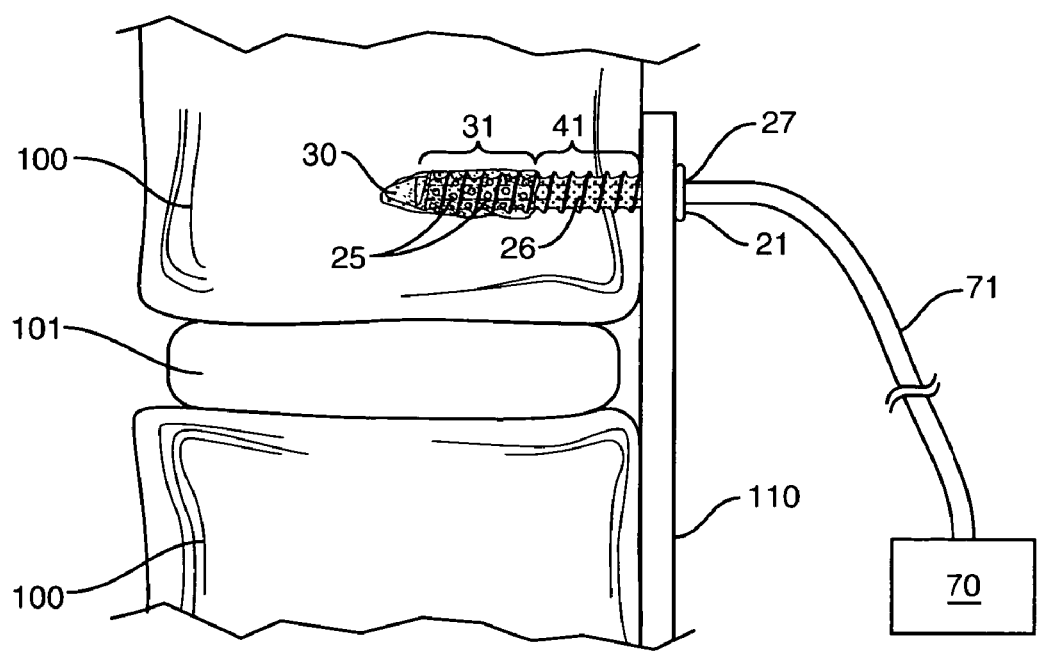
Figure 8D:
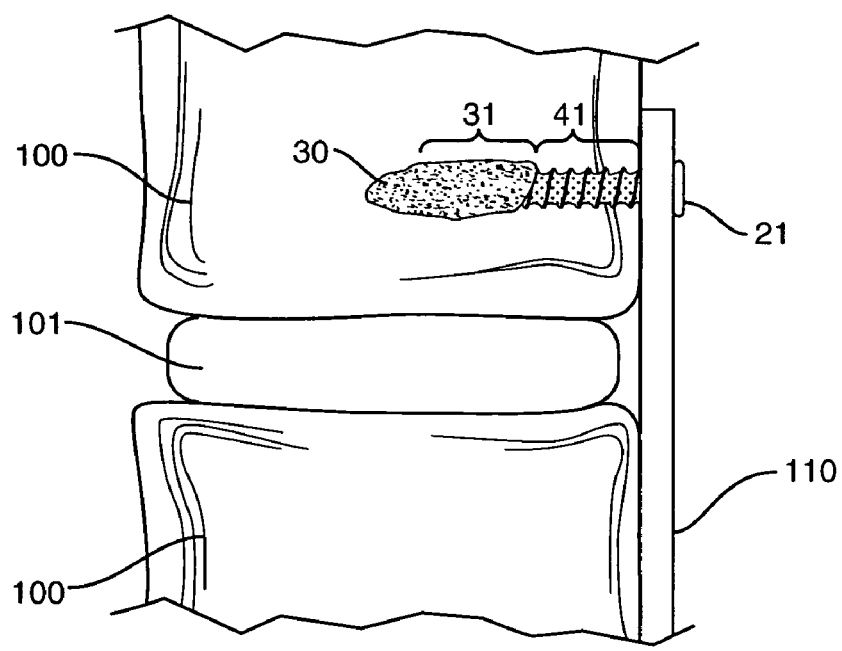

After the fastener 20 is inserted within the vertebral member 100, the bone void filling material 30 is delivered to the bone void filling section 31. In the embodiment of FIG. 8C, a pump 70 with a conduit 71 is attached to the inlet 27 in the head 21. Pump 70 is activated and bone void filling material 30 is delivered into the channel 26 and through the openings 25 and into contact with the vertebral member 100. The pump 70 is deactivated and the conduit 71 is removed from the fastener 20.

The threads 24 bite into the vertebral member 100 and provide immediate mechanical anchoring. The bone void filling material 30 is further delivered to augment the mechanical anchoring within the vertebral member 100. The osteogenic material 40 improves bony apposition at the proximal section of the shaft 22 which fosters long-term anchoring of the fastener 20.

A variety of different fasteners 20 may be used with the present application. Examples include threaded screws, rivets, and pins. The fasteners 20 may further be constructed of a variety of materials that may be permanent, semi-permanent, or bio-resorbable. Examples of permanent materials include stainless steel, titanium, and plastic. Semi-permanent materials include magnesium, hydroxyapatite, and hydroxyapatite-polymer composite. Bio-resorbable material examples include PLA, PLDLA, polyorthoester, and tyropolycarbonate.

The embodiment of FIG. 1 illustrates the fasteners 20 mounted to a posterior side of a vertebral member. FIGS. 8A-8D illustrate an embodiment mounted to an anterior side. The fasteners 20 are applicable to the various regions of the spine, including the cervical, thoracic, lumbar and/or sacral regions. In addition, fasteners 20 are also applicable as anchors within other areas of a patient.

The term "distal" is generally defined as in the direction of the patient, or away from a user of a device. Conversely, "proximal" generally means away from the patient, or toward the user. Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A surgical fastener comprising:
    a body comprising head, a tip at a distal end and a helically threaded shaft extending between the head and the distal end, the shaft including a longitudinal distal section and a longitudinal proximal section, the shaft being formed of a first material;
    a channel extending through an interior of the head and the shaft;
    a helical array of openings positioned between the threads on the shaft in communication with the channel, the channel and the openings being sized to deliver bone void filling material to the distal section of the shaft, the openings being limited to the distal section and spaced away from the proximal section; and
    an osteogenic material comprising a PEG/PLL copolymer attached to the threads of the proximal section of the shaft;
    the distal section being devoid of the osteogenic material with the first material of the shaft being exposed.

2. The fastener of claim 1, wherein the openings are spaced away from the tip.

3. The fastener of claim 1, wherein a longitudinal length measured along the shaft of the distal section and the proximal section are substantially equal.

4. The fastener of claim 1, wherein the osteogenic material is hydroxyapatite.

5. The fastener of claim 1, wherein the osteogenic material is osteo-inductive.

6. The fastener of claim 1, wherein the osteogenic material is osteoconductive.

7. The fastener of claim 1, wherein the osteogenic material further comprises a pharmaceutical agent.

8. The fastener of claim 1, further comprising a second osteogenic material attached to the shaft at a section that is spaced apart from the osteogenic material.

9. The fastener of claim 1, wherein each of the openings is positioned equidistant between two adjacent threads on the shaft.

10. The fastener of claim 1, wherein the osteogenic material is a PEG/PLL copolymer having a molecular weight greater than 300.

11. The fastener of claim 1, wherein the osteogenic material is a PEG/PLL copolymer having structures that include AB copolymers, ABA copolymers, brush-type copolymers, or combinations thereof.

12. A surgical fastener comprising:
a body comprising a head, a tip at a distal end, and a threaded shaft between the head and the distal end;
a distributing network comprising a channel extending through an interior of the body and openings within the shaft that extend from the channel to distribute a bone void filling material, the openings positioned along a distal section of the shaft away from a proximal section of the shaft;
an osteogenic material attached to the threads of the proximal section of the shaft away from the openings in the distal section of the shaft
wherein the osteogenic material is a PEG/PLL copolymer.

13. The fastener of claim 12, further comprising a second osteogenic material attached to the shaft at a section that is spaced apart from the osteogenic material.

14. The fastener of claim 12, wherein the osteogenic material is hydroxyapatite.

15. The fastener of claim 14, wherein the hydroxyapatite is coated to the shaft.

16. The fastener of claim 12, wherein the osteogenic material is osteo-conductive.

17. The fastener of claim 12, wherein the osteogenic material is osteo-inductive.

18. A method of attaching a fastener within a vertebral member, the method comprising the steps of:
inserting the fastener into the vertebral member by rotating the fastener and causing threads on a shaft to bite into the vertebral member with the threaded shaft extending into an interior of the vertebral member and a head at the proximal end of the shaft extending outward from the vertebral member, the fastener being made of a first material;
contacting an osteogenic material comprising a PEG/PLL copolymer coated onto threads of a proximal section of the shaft with cortical bone tissue positioned along a periphery of the vertebral member, and contacting the first material that is exposed along an intermediate section of the fastener with cancellous bone tissue within the interior of the vertebral member;
delivering bone void filling material to the cancellous bone tissue within the interior of the vertebral member by distributing the bone void filling material through a channel within the shaft and through openings in a distal section of the shaft; and
spacing apart the bone void filling material from the osteogenic material by the intermediate section of the shaft that is not coated with the osteogenic material and is positioned between the proximal and distal sections.

* * * * *